United States Patent [19]

Stewart et al.

[11] Patent Number: 5,304,631
[45] Date of Patent: Apr. 19, 1994

[54] SYNTHETIC HELIZYME ENZYMES

[75] Inventors: John M. Stewart, Denver; Karl W. Hahn, Englewood; Wieslaw A. Klis, Denver, all of Colo.

[73] Assignee: University of Colorado Foundation, Inc., Boulder, Colo.

[21] Appl. No.: 464,932

[22] Filed: Jan. 16, 1990

[51] Int. Cl.$^5$ .......................... C07K 7/02; C07K 7/00; C12N 9/76; C12N 9/18
[52] U.S. Cl. .................................. 530/323; 530/324; 530/300; 530/350; 435/213; 435/219; 435/197
[58] Field of Search ............... 530/350, 300, 323, 324; 435/213, 68.1, 219, 197

[56] References Cited

PUBLICATIONS

Craik et al. "The Catalytic Role of the Active Site . . ." *Science* vol. 237 p. 909 Aug. 21, 1987.
Regan et al. (1988) Science 241:976-978.
Mutter (1988) TIBS 13:260-265.
Mutter and Tuchscherer (1988) Makromol. Chem. Rapid Commun. 9:437-443.
Mutter et al. (1988) Tetrahedron 44:771-785.
Mutter et al. (1988) Helvetica Chimica Acta 71:835-846.
Mutter et al. (1989) Proteins: Structure, Function, and Genetics 5:13-21.
Mutter and Vuilleumier (1989) Angew. Chemie (Intl ed.) 28:535-679.
DeGrado et al. (1989) Science 243:622-628.
Sasaki and Kaiser (1989) J. Am. Chem. Soc. 111:380-383.
Mutter (1985) Angew. Chem. Int. Ed. Engl. 24:639-653.
Vorherr et al. (1986) Helv. Chim. Acta 69:410-414.

*Primary Examiner*—Robert A. Wax
*Assistant Examiner*—Keith D. Hendricks
*Attorney, Agent, or Firm*—Greenlee and Winner

[57] ABSTRACT

The design, and synthesis of peptide-based molecules termed helizymes which possess catalytic activity are described herein The catalytic molecules of the invention comprise a number of amphiphilic helical peptides, which interact via hydrophobic interactions and which are bonded at their carboxyl ends to a multifunctional base. Active site residues functional for catalysis are positioned within or at the N-termini of the helical peptides. The helizyme molecule adopts a conformation in aqueous medium such that a substrate binding pocket is formed and such that functional active site geometry results from the association of the helical peptides Specifically exemplified helizymes possess specificities and at least one catalytic activity of chymotrypsin, trypsin and acetylcholine esterase.

5 Claims, 2 Drawing Sheets

SYNTHETIC HELIZYME ENZYMES

This work was supported by a grant from the United States Government funded through the Office of Naval Research. The United States Government has certain rights in this invention.

FIELD OF THE INVENTION

The field of this invention is protein chemistry and enzyme engineering, particularly the production of peptide-containing molecules with enzyme-like catalytic activity.

BACKGROUND OF THE INVENTION

Much is now known about the correlation between the amino acid sequence, or primary structure, of a protein and its secondary structure. This knowledge allows some predictions to be made about the energetically favored conformations that a protein of known amino acid sequence will assume in an aqueous solvent. The basic building blocks of protein secondary structure are the α-helix, the β-sheet and the β-turn. Chou et al. (1974) Biochemistry 13:211, 222; Chou et al. (1978) Ann. Rev. Biochem. 47:251-278; and Fasman (1987) Biopolymers 26(supp.):S59-S79 have shown that certain amino acids have a propensity for forming α-helices, while others tend to destabilize helices. One turn of the α-helix contains 3.6 amino acids, and is stabilized in part by hydrogen bonding interactions between amino acid residues and by interactions between neighboring amino acid residues such as vertical ionic bonding between negatively and positively charged amino acids. Helix-forming amino acids include Glu, Ala, His, Leu, Asp, Met, Ser, Lys, Arg, Phe and Trp (see Table 1 for amino acid one letter and three letter codes). Amino acids associated with β-turns and β-pleated sheets are also known. For additional reviews of the relationship between amino acid sequence and secondary structure, see Richardson and Richardson (1988) Science 240:1648-1652; presta and Rose (1988) Science 240:1632-1641; and Garnier et al. (1978) J. Mol. Biol. 120:97-120. Molecular modeling programs are known in the art which allow predictions of at least portions of the favored secondary structure of amino acid sequences. DeLisi (1988) Science 240:47-52 and von Heijne (1988) Nature 333:605-607 give some discussion of publicly-available software for the analysis of amino acid data.

TABLE 1

| ABBREVIATIONS AND CONVENTIONS USED | |
|---|---|
| ATEE | N-Acetyl-L-tyrosine ethyl ester |
| Boc | t-Butyloxycarbonyl |
| Bom | Benzyloxymethyl |
| Bzl | Benzyl |
| BTEE | N-Benzoyl-L-tyrosine ethyl ester |
| DCM | Dichloromethane |
| Clz | 2-Chlorobenzyloxycarbonyl |
| Fmoc | 9-Fluorenylmethoxycarbonyl |
| MBHA | p-Methylbenzhydrylamine resin (for synthesis of peptide amides) |
| Npys | 3-Nitro-2-pyridylsulfenyl |
| Tos | p-Toluenesulfonyl |
| TFA | Trifluoroacetic acid |
| ZTONP | N-Benzyloxycarbonyl-L-tyrosine p-nitrophenyl ester |

Common Amino Acids

| | 3 letter | 1 letter | | 3 letter | 1 letter |
|---|---|---|---|---|---|
| Alanine | Ala | A | Lysine | Lys | K |
| Arginine | Arg | R | Methionine | Met | M |
| Asparagine | Asn | D | Ornithine | Orn | |

TABLE 1-continued

| ABBREVIATIONS AND CONVENTIONS USED | | | | | |
|---|---|---|---|---|---|
| Aspartic Acid | Asp | D | Phenylalanine | Phe | F |
| Cysteine | Cys | C | Proline | Pro | P |
| Glutamic Acid | Glu | E | Pryoglutamyl | <Glu | <E |
| Glutamine | Gln | Q | Serine | Ser | S |
| Glycine | Gly | G | Threonine | Thr | T |
| Histidine | His | H | Tryptophan | Trp | W |
| Isoleucine | Ile | I | Tyrosine | Tyr | Y |
| Leucine | Leu | L | Valine | Val | V |

Representation of blocking groups on amino acids:
A symbol to the left and hyphenated is a blocking group on the α-amino group: Boc—Gly=N-α-Boc—glycine.
A symbol to the right and hyphenated is an ester on the α-carboxyl: Gly—OHBT=hydroxybenzotriazole ester of glycine.
A symbol after the amino acid symbol and in parentheses is a blocking group on the side chain: Tyr(Bzl)=O—benzyl tyrosine.
EXAMPLES: Boc—Glu(OBzl)—ONp=ONp=N-α-Boc glutamic acid - gamma benzyl ester α-nitrophenyl ester, Boc—Tyr(Bzl)—OBzl=N-α-Boc—O—Benzyl—tyrosine benzyl ester.

Interactions between structural components within a protein and the interactions between these structural components and the solvent environment determine the preferred tertiary structure of a protein. Hydrophobic interactions, especially in the internal portions of the protein, are particularly important in determining the most favorable conformation. For example, amphiphilic α-helices, in which the amino acids are positioned such that the helix contains a hydrophobic and a hydrophilic face, will interact to form tight bundles In such structures, the hydrophobic faces of the α-helices associate, while the hydrophilic faces of the helices at the surface of the structure interact with aqueous solvent. Similarly, if there are two β-pleated sheet structures in which hydrophobic and hydrophilic amino acid residues alternate, the sheets may lie over one another, held by the interactions of the hydrophobic faces of the sheets. The interaction of secondary structure features of proteins is also influenced by the size of the amino acid side chains present and the possible formation of hydrogen bonds, salt bridges and covalent disulfide bonds.

One of the important principles of protein structure is that there is degeneracy in the folding code, i.e. different sequences can interact to form similar secondary structures and similar overall tertiary structures. In other words, the possible conformations for proteins are not equal to the number predicted statistically. Thus, it is practical to use the principles of secondary and tertiary structure to generate at least a simple model protein structure. There have been several reports of successful attempts to model a desired protein structural feature.

Regan et al. (1988) Science 241:976-978 detail the de novo design of a helical protein containing 74 amino acids, which design employed information known about the factors which stabilize amino acid α-helices. The model protein design included four identical α-helical regions connected by three identical hairpin loop regions and was intended as an idealized version of the naturally occurring four-helix bundle motif of myohemerythrin and cytochrome c'. A nucleic acid sequence which encoded the designed polypeptide was synthesized and combined with the tac promoter to form a synthetic gene which was then expressed in E. coli to form the designed protein. The helix-forming peptide sequence employed (-Gly-Glu-Leu-Glu-Glu-Leu-Leu-Lys-Lys-Leu-Lys-Glu-Leu-Leu-Lys-Gly)

was designed to be amphiphilic so that in the complete protein a four-helix bundle would form with hydrophobic amino acids residues interacting at its interior and hydrophilic amino acid residues directed outward into the aqueous solvent. The hydrophilic residues glutamate and lysine were arranged in the sequence so that they could form ion-pairs along one face of the helix. In addition, each helical region contained negatively charged residues at its amino terminus and positively charged residues at the carboxy terminus to further stabilize helix formation. The specific hairpin loop sequence which was employed to separate the helical regions was: -Pro-Arg-Arg-. Circular Dichroism (CD) measurements of the resultant designed protein in aqueous solution indicated that it was predominantly α-helical in structure and size exclusion chromatography indicated the protein was monomeric. No particular function was associated with the designed protein.

Mutter and co-workers (see Mutter (1988) TIBS 13:260-265; Mutter and Tuchscherer (1988) Makromol. Chem. Rapid Commun. 9:437-443; Mutter et al. (1988) Tetrahedron 44:771-785; Mutter et al. (1988) Helvetica Chimica Acta 71:835-846; Mutter et al. (1989) Proteins: Structure, Function, and Genetics 5:13-21; Mutter and Vuilleumier (1989) Angew. Chemie (Intl Ed.) 28:535-679) have described the concept of the template-associated synthetic protein (TASP). In a TASP, component amphiphilic peptides, particularly those preferring α-helical and β-sheet structures, are assembled by covalent bonds to a carrier or template molecule which is said to direct "the peptide chains into protein-like packing arrangements." The resultant molecule has a branched structure in which a number of peptides extend from the template. Oligopeptides, in particular, are employed as template molecules. In these TASPs, as in the 4-helix bundle molecule of Regan et al. supra, the component peptide chains each have identical amino acid sequences.

In nature, protein molecules have a variety of functions. One of the most important and most intensely studied functions of proteins is as enzymes. Enzymes catalyze chemical reactions of their substrates. An enzyme's properties are ultimately determined by its amino acid sequence, i.e. its primary structure. The primary structure directs the formation of any secondary structure and the overall three-dimensional or tertiary structure of the protein. The three-dimensional structure of the protein specifies the relational geometry of the amino acids which are associated with the active site (amino acid residues involved in catalysis), and determines the structure and composition of any substrate binding site. The structural characteristics of an enzyme protein establish the reaction catalyzed, any substrate specificity or selectivity of the reaction catalyzed and the kinetics of that reaction.

There is growing interest in the design of synthetic, small molecule enzymes to carry out known enzymatic reactions. Such synthetic catalysts are desirable because it is believed that a number of the problems associated with the use of enzyme catalysts, such as instability, can be alleviated while the desirable high selectivity and reaction rates of enzymes can be retained. In addition, an understanding of the correlation between an enzyme's structure and its properties, such as substrate specificity, can be employed to create enzyme-like catalysts having unique properties. For medical applications, there may be additional benefits resulting from the expected lower immunogenicity of low molecular weight synthetic enzymes. Furthermore, the ability to synthesize an enzyme chemically avoids any possible problems in isolating the enzyme in pure form from its natural source or in expression problems associated with production by recombinant DNA techniques. Several strategies have been employed to achieve artificial enzyme activity. Attempts have been made to mimic the substrate binding ability of the enzyme and/or mimic an enzyme active site and thus obtain catalytic activity.

Breslow et al. (1988) Tetrahedron 44:5515-5524 have described a strategy to obtain enzyme-like selective substrate binding in a relatively small molecule. Pyridoxamine phosphate, the cofactor commonly associated with transaminase enzymes, was covalently attached to β-cyclodextrin to produce a substrate selective reactant. The α-keto amino acids phenylpyruvic acid and indolepyruvic acid were selectively bound via their aromatic rings in the cyclodextrin cavity, and were converted to phenylalanine and tryptophan, respectively, by reaction with the bound co-factor. In contrast, the pyridoxamine-cyclodextrin did not react with pyruvate to form alanine. Substrate specificity of the reaction is said to result from binding of the aromatic ring of the α-keto acid in the cyclodextrin cavity. In enzyme catalyzed transaminase reactions, pyridoxamine phosphate is regenerated by amino group transfer from a different amino acid (resulting in transamination). The pyridoxamine-cyclodextrin reactant described is not regenerated after reaction and is therefore not a true catalyst.

Kelly et al. (1989) J. Am. Chem. Soc. 111:3744-3745 have described a bi-substrate reaction template molecule, which brings two substrate molecules in close proximity and thus accelerates the reaction between them. The template molecule, which is composed of linked aromatic rings, was specifically designed to contain binding sites for desired substrates. The binding sites contain amine and keto groups selected for interaction with a specific substrate.

Poly-α-amino acids have been described which act as stereospecific catalysts for epoxidation reactions (Valencia-Parera et al. (1986) J. Coll. Interface Sci. 114:140-148). Polyalanine and chalcone were shown to interact in a water-toluene emulsion in the presence of air to produce an asymmetric epoxychalcone. The mechanism by which stereospecificity is achieved is not understood, but is suggested to be related to the kind of emulsion formed.

A protein with ion channel activity has been designed which contains four antiparallel helices (DeGrado et al. (1989) Science 243:622-628). The amino acid sequence of the protein specifies the four helical regions, which are separated by amino acid sequences which have the requisite flexibility for appropriate folding. The helices are designed so that the "outsides" of the helices are hydrophobic to facilitate positioning within lipid bilayers, and the "insides" of the helices are hydrophilic so that proton-conductive channels are formed when the four helices associate. The bulkiness of the amino acid groups at the interior of the bundle structure prevents the conductance of larger cations.

The synthesis and enzyme-like activity of a designed hemeprotein called a helichrome has been described (Sasaki and Kaiser (1989) J. Am. Chem. Soc. 111:380-383). The helichrome is composed of four identical amphiphilic α-helices bound to a porphyrin ring to which Fe(III) can be complexed. The four helices, each of which has the amino acid sequence: Ala-Glu-Gln- Leu-Leu-Gln-Glu-Ala-Glu-Gln-Leu-Leu-Gln-Glu-Leu-amide, are reported to interact to form a hydrophobic pocket in aqueous solution into which a substrate can bind. The Fe(III) helichrome complex was reported to catalyze the hydroxylation of aniline to p-aminophenol. The kinetic constants of the helichrome-catalyzed hydroxylation of aniline are similar to those observed for the same reaction catalyzed by hemoglobin, indoleamine 2,3-dioxygenase and L-tryptophan 2,3-dioxygenase.

The serine proteases are a family of extensively studied enzymes which catalyze similar reactions (the hydrolysis of peptide and certain ester bonds) and share common structural features in their active site. The serine proteases, which include among others chymotrypsin, trypsin and elastase, are so named because of the presence of a uniquely reactive serine residue at their active site. Even though the amino acid sequences of chymotrypsin, trypsin and elastase are quite different, the enzymes have a very similar tertiary structure. Each contains a similar active site composed of an Asp, His and Ser (positions 102, 57 and 195 in chymotrypsin) in an approximately planar arrangement which form a "charge relay system." The serine proteases also have a substrate binding pocket allowing appropriate positioning of the substrate with respect to the active site. Differences in the structure of the substrate binding pocket of serine proteases are associated with differences in substrate specificity. Because the active site structure and mechanism of catalysis by serine proteases are well understood, several attempts have been made to create artificial enzymes which mimic their catalytic activities.

Mutter (1985) Angew. Chem. Int. Ed. Engl. 24:639-653 reviews several apparently unsuccessful strategies that have been applied in order to mimic α-chymotrypsin activity. He notes that chymotrypsin "mimics" produced by polymerization of the amino acids of the active site resulted in low catalytic activity probably due to the random structure of the polypeptides. He further notes that cyclic peptides containing the active site amino acids, such as cyclo-(Gly-L-His-L-Ser-Gly-L-His-Ser-) display no significant enhancement of hydrolysis of the chymotrypsin substrate, p-nitrophenyl acetate. He then reports the synthesis of the peptide:

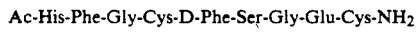

Ac-His-Phe-Gly-Cys-D-Phe-Ser-Gly-Glu-Cys-NH$_2$ which is described as having functional groups oriented by a β-turn and an S—S bond and having a hydrophobic pocket provided by the two phenylalanine residues. The peptide, however, is described as having "low catalytic activity."

Vorherr et al. (1986) Helv. Chim. Acta 69:410-414 described a single-center model for the active site of α-chymotrypsin. The model utilizes the hydrophilic polymer polyethyleneglycol (PEG) to which a peptide containing amino acid residues similar to those of the active site of α-chymotrypsin was attached. In the specific model, glutamate was substituted for aspartate for convenience in synthesis of the peptide. The specific sequence of the peptide employed, Glu-Gly-His-Pro-Gly-Ser-Gly, was predicted to have a high potential for β-turn configuration. It was also predicted that a preferred conformation of the peptide would contain a planar H-bonded structure involving the side chains of Glu, His and Ser which would approximate the interactions of Asp-102, His-57 and Ser-195 in the active site of native chymotrypsin. CD measurements were reported to confirm that the PEG-bound peptide was predominantly in the β-turn conformation which the authors suggest indicates that the active site residues are in the proper geometry for activity. The PEG-bound peptide was, however, reported to display "no increased catalytic activity . . . compared to other functional model compounds . . . in the hydrolysis of p-nitrophenylacetate."

Thus, while some success in modeling desired peptide and protein structures has been achieved, much less success has been achieved in mimicking the function of proteins such as enzymes.

SUMMARY OF THE INVENTION

The present invention describes the design and synthesis of peptide molecules which possess catalytic activity. The design employs knowledge available to the art regarding the correlation of primary, secondary and tertiary structure of peptides and proteins to construct a chosen active site geometry. In addition, the chosen active site can be positioned with respect to a specifically designed substrate binding structure to achieve a desired substrate specificity.

It is an object of this invention to provide a catalyst having at least one of the catalytic activities of a selected enzyme, which catalyst is comprised of a plurality of amphiphilic helical peptides, bonded at their carboxyl ends to a multifunctional base framework and having the active site residues of the enzyme positioned within the helices, with primary, secondary and tertiary structure such that a functional enzyme catalytic site, similar to that of the selected enzyme, is formed. The helices of the catalyst adopt a preferred conformation in aqueous solution such that a substrate binding pocket is formed. The size and chemical environment of the substrate binding pocket can be modified by appropriate choice of amino acid residues to selectively vary the specificity of the binding site.

The catalyst of the present invention, designated herein a helizyme, has at least one catalytic activity of a selected enzyme, and has substrate specificity. The schematic structure of the helizymes of the present invention are exemplified by the structure of FIG. 1. The substrate specificity of the helizyme may be similar to or substantially that of the selected enzyme. Alternatively, the substrate binding pocket can be modified to achieve a desired binding specificity which need not be that of a native enzyme. In certain preferred embodiments the substrate binding pocket of the helizyme is hydrophobic in nature. It is preferred that the desired active site residues are positioned at or near the amino termini of the amphiphilic helices of the peptide. Not all of the amphiphilic helices of the helizyme need contain an active site residue. One or more of the helices can be designed to contain amino acid residues which taken together provide a structural or chemical feature which is essential for or enhances catalytic function. An example of such a feature is an "oxyanion hole" which has been described in serine proteases and which is implemented in the specific embodiments of the present invention.

The amino acid sequence of the helices is chosen such that the desired geometry of the active site residues can be obtained in the helizyme. Additionally the amino acids of the helices are chosen to obtain the desired structure and chemical composition of a substrate binding site which is formed on their interaction. In general, the helices in a helizyme will not all have identical amino acid sequences. It is preferred that the N-terminus of each helical peptide is blocked by an acyl group, which further stabilizes helix formation. Suitable acyl groups include among others acetyl, propionyl, and succinyl groups. The amphiphilic helices of the helizyme can also contain cysteine residues which allow the formation of one or more disulfide bonds between the helices. The substrate binding pocket of a helizyme can be modified by inclusion of specific amino acids which will be positioned within the pocket to allow specific binding to a desired substrate. For example, the substrate binding pocket can be modified by introducing an acidic amino acid, such as aspartic acid, at the bottom of the pocket. Such a modification will provide substrate binding specificity for positively charged groups, as is found in trypsin or acetyl choline esterase. The size of the substrate binding pocket can also be modified by positioning of amino acids with large or small side chains or by increasing or decreasing the number of helices. Preferably, each amphiphilic helical peptide of the helizyme contains from about 10 to about 25 amino acid residues.

More specifically, helizymes in which the amphiphilic helical peptides contain active site residues of a protease such as a serine protease, including among others chymotrypsin, trypsin, elastase, acetyl choline esterase, thrombin, plasmin and the bacterial serine proteases such as subtilisin; a thiol protease, including among others papain, ficin, bromelain and bacterial thiol proteases; or an acid protease including among others pepsin, renin, cathepsin D and penicillopepsin can be constructed. Helizymes having at least one catalytic activity of a protease, particularly of a serine protease, a thiol protease or an acid protease can be constructed employing the descriptions and methods of the present invention.

In a preferred embodiment, a helizyme having the active site residues of a serine protease is described. In this preferred embodiment, a hydrophobic substrate binding pocket can be formed by interaction of the amphiphilic helices in aqueous solution. Specifically, a helizyme in which four amphiphilic helical peptides are linked to ornithine substituted with lysine at the base of the molecule and in which those peptides interact to form a functional substrate binding site and a functional serine protease-like active site, is presented. Designs for substrate binding sites or pockets with different substrate specificities are provided. In particular, a substrate binding site or pocket which is specific for large hydrophobic groups such as aromatic rings is presented.

In addition, substrate binding sites specific for certain positively charged groups are presented.

A specific embodiment of a helizyme with catalytic activities similar to that of a serine protease and substrate specificity similar to that of chymotrypsin is Chymohelizyme 1 (CHZ-1), which has the primary structure shown in Table 2 and the predicted tertiary structure (in aqueous solution) displayed in FIG. 2. CHZ-1 has esterase activity similar to that of native chymotrypsin, and it shows a preference for substrates similar to that observed for native chymotrypsin.

A second specific embodiment of an artificial serine protease-like helizyme with specific substrate specificity similar to that of chymotrypsin, is Chymohelizyme 2 (CHZ-2), in which two of the component amphiphilic helical peptides are covalently linked by a disulfide bond between cysteine residues. The primary structure of CHZ-2 is given in Table 3. The helices of CHZ-2 contain cysteine residues between which a disulfide bond can be formed to confer additional conformational stability and decrease the dimer formation in aqueous solution.

TABLE 2A

Chemical Schematic Structure of a Chymohelizyme.*

*Amino acid residues are numbered so that the catalytic triad (His, Asp, Ser) resides correspond with chymotrypsin sequence numbers. Other residues are given numbers following those of the catalytic residues at the N-termini of the peptides. The Glu chain has no exact correspondence in chymotrypsin. This peptide helps to stabilize the structure and to furnish the necessary "oxyanion hole" for the catalytic mechanism. The Glu chain is arbitrarily numbered beginning with 1.

TABLE 2B

Amino Acid Sequences of the Peptide Chains of Chymohelizyme 1.

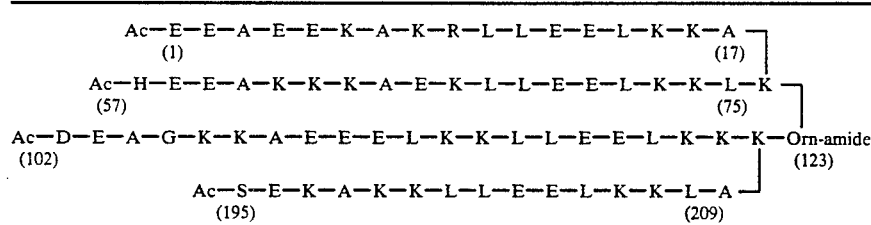

TABLE 3A

Chemical Schematic Structure of Chymohelizyme 2.*

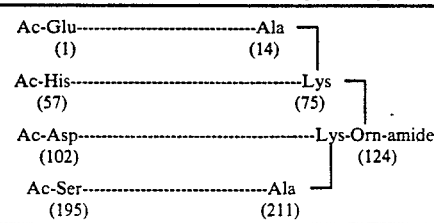

TABLE 3B

Amino Acid Sequences of the Peptide Chains of Chymohelizyme 2.*

```
       Ac—E—E—L—E—K—E—C—K—R—L—K—K—A ┐
       (1)                          (14) │
                                          │
   Ac—H—E—E—L—L—K—K—L—K—E—L—L—K—K—L—E—K—K ┐
   (57)                                  (75) │
                                              │
Ac—D—E—E—L—K—K—L—E—E—E—A—K—K—L—E—E—L—K—K—K—Orn-Amide
(102)                                        │ (124)
                                              │
       Ac—S—E—E—E—E—K—K—A—K—E—K—A—C—K—E—L—A ┘
       (195)                                (211)
```

*The two cysteine (C) residues (#7 in the Glu chain and #207 in the Ser chain) are positioned so that when the 4-bundle helix assumes the correct conformation they are directly apposed so as to form a disulfide bond to hold the structure firmly in place. Numbering of residues is as in Table 2.

A further preferred embodiment of the present invention is that of a helizyme with enzymatic activity like that of trypsin, termed herein a tryptihelizyme. A plurality of amphiphilic helical peptides, preferably four, at least three of which have the Ser, His and Asp active site residues characteristic of a serine protease at or near their amino ends, and all of which are attached at their carboxyl ends to a multifunctional base molecule, interact to form a substrate binding pocket which confers the preferred substrate specificity of native trypsin. l0 One or more of the helices incorporates at least one acidic amino acid which functions in specific binding to basic amino acids in trypsin substrates. The tertiary structure of the molecule confers the relational geometry of the serine protease active site, so that the preferred substrate specificity and at least one catalytic activity of native trypsin are expressed by the trypsin-like helizyme. A specific embodiment of a tryptihelizyme is the molecule having the primary structure which is given in Table 4.

which is given in Table 5B. In this helizyme the catalytic site is analogous to that of the Chymohelizymes and Tryptihelizymes, but the substrate binding site has been modified to fit acetyl choline. This helizyme provides a new method for treatment of victims of poisoning by nerve gas or by phosphate insecticides. Helizymes having acetyl choline esterase catalytic activity can be employed to eliminate toxic levels of acetyl choline (i.e. reducing acetyl choline to non-toxic levels in the body). These cholihelizymes can be administered directly to patients, for example by intravenous injection, or can be employed extracorporeally. For example, an immobilized cholihelizyme can be employed in an extracorporeal circulation device to reduce levels of circulating acetyl choline.

TABLE 5

Amino Acid Sequence of the Peptide Chains of Cholihelizyme 1.

```
       Ac—E—E—A—E—E—K—A—K—R—D—L—E—E—L—K—K—A ┐
       (1)                                 (17) │
                                                │
   Ac—H—E—E—A—K—K—K—A—E—K—L—L—E—E—L—K—K—L—K ┐
   (57)                                   (75) │
                                               │
Ac—D—E—A—G—K—K—A—E—E—L—K—K—L—L—E—E—L—K—K—K—Orn-amide
(102)                                         │ (123)
                                               │
           Ac—S—E—K—A—K—K—L—L—E—E—L—K—K—L—A ┘
           (195)                            (209)
```

The artificial enzymes of the present invention may also be embodied in forms in which the structure of the base supporting group is modified so that the helizymes can be immobilized on a solid support, as is understood in the art. This feature is specifically embodied within

TABLE 4

Amino Acid Sequence of the Peptide Chains of Tryptihelizyme 1.

```
       Ac—E—E—A—E—E—K—A—K—R—L—L—E—E—L—K—K—A ┐
       (1)                                 (17) │
                                                │
   Ac—H—E—E—A—K—K—K—A—E—K—L—L—E—E—L—K—K—L—K ┐
   (57)                                   (75) │
                                               │
Ac—D—E—A—G—K—K—A—E—E—L—K—K—L—L—E—E—L—K—K—K—Orn-amide
(102)                                         │ (123)
                                               │
           Ac—S—E—K—A—K—K—D—L—E—E—L—K—K—L—A ┘
           (195)                              (209)
```

A further preferred embodiment of the present invention is that of a helizyme with enzymatic activity like that of acetyl choline esterase (AChE). AChE is the enzyme essential for physiological muscle relaxation, and is the enzyme poisoned by phosphate nerve gases and phosphate insecticides. AChE has the typical serine protease catalytic triad of active site residues, His, Ser and Asp. A specific embodiment of a cholinesterase helizyme is the molecule having the primary structure the modified structure of Chymohelizyme 2 as shown in Table 6. The structure shown in Table 6A, containing a methionine residue near the carboxyl end of the Asp chain, is treated with cyanogen bromide to activate the structure for reaction of the homoserine lactone (see Table 6B) with amine-functionalized solid supports.

The size of the synthetic enzymes of the present invention is small enough so that it is practical to utilize automatic solid phase peptide synthetic techniques to produce them. The specially designed helizymes of the present invention will have advantages over native enzymes such as increased stability to denaturation, degradation and aggregation. It is also anticipated that synthetic enzymes such as those described herein may be useful in medical procedures and treatments, and may offer additional advantages over naturally occurring materials such as theoretically unlimited supply and lower immunogenicity. It is also anticipated that helizymes, particularly in their immobilized embodiments, will be useful in the transformation of commercial process streams.

TABLE 6A

Chemical schematic structure of chymohelizyme 2 adapted for immobiliztion.*

```
Ac-Glu----------------------Ala ┐
  (1)                       (14) │
Ac-His---------------------------Lys ┐
  (57)                           (75) │
Ac-Asp-------------------------------Lys-Orn-Met-Gly-amide
  (102)                                      (126)
Ac-Ser--------------------------Ala ┘
  (195)                        (211)
```

*The amino acid sequence of the component peptides is the same as that of CHZ-2, as given in Table 3B.

TABLE 6B

Schematic structure of Chymohelizyme 2 modified for immobilization after activation with cyanogen bromide to convert Met-125 to the homoserine lactone.*

```
Ac-Glu----------------------Ala ┐
  (1)                       (14) │
Ac-His---------------------------Lys ┐
  (57)                           (75) │
Ac-Asp-------------------------------Lys-Orn-Hse-lactone
  (102)                                      (125)
Ac-Ser--------------------------Ala ┘
  (195)                        (211)
```

*The amino acid sequence of the component peptides is the same as that of CHZ-2, as given in Table 3B.

Specifically, the present invention provides a method of treatment of conditions which result in a toxic excess of acetyl choline. A toxic excess of acetyl choline results, for example, from poisoning by alkyl phosphates such as those which are employed in insecticides and nerve gas.

It is also an object of the present invention to provide methods for carrying out chemical reactions employing the catalytic molecules described herein.

BRIEF DESCRIPTION OF THE FIGURES

FIG. 1, Panel A. Side view, with Glu-1 and Ser-195 chains in the foreground. N-terminals are at the top; C-terminals at the bottom. Amino acid residues at the ends of the chains are labeled. Van der Waals shells are added to the substrate and the catalytic triad residues in the enzyme. FIG. 1, Panel B. End view with the catalytic site in the foreground. N-terminal residues are labeled. The aromatic ring of the substrate appears just to the left of the ring of the catalytic histidine in the enzyme.

DETAILED DESCRIPTION OF THE INVENTION

Figure 1:
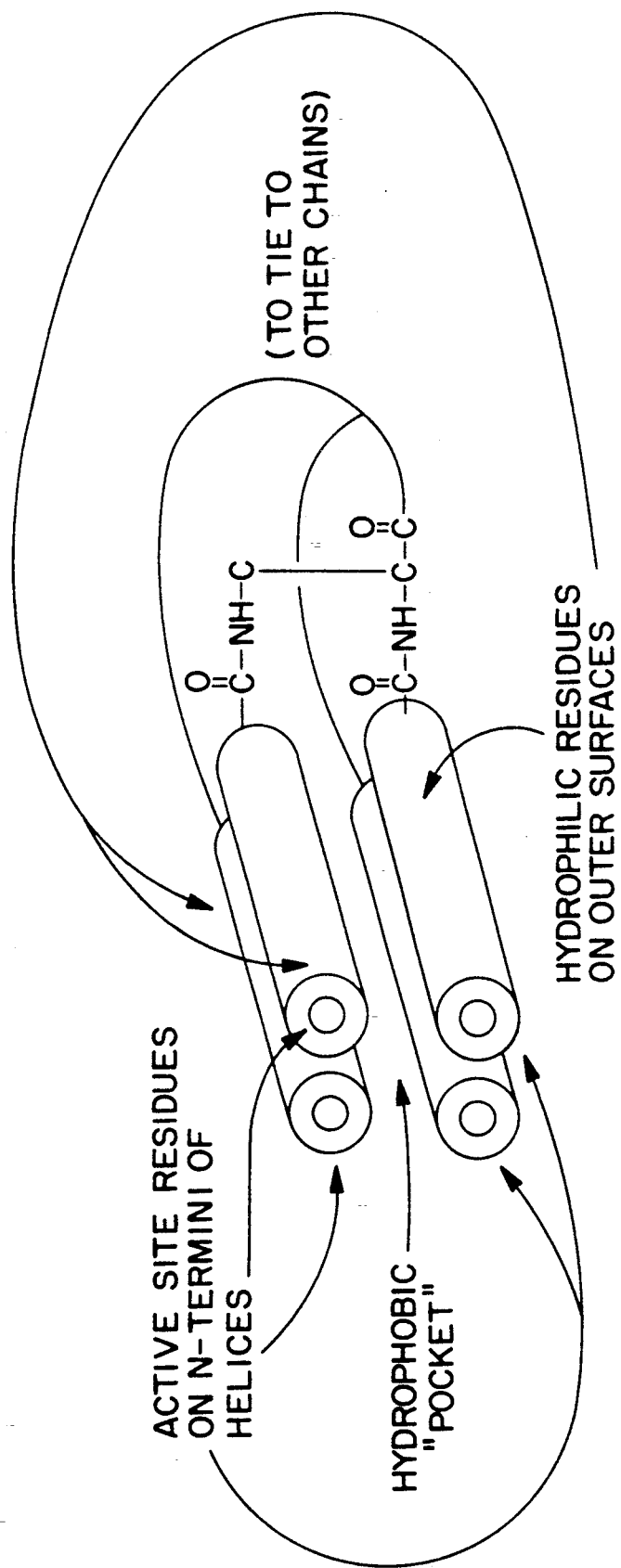
FIG. 1 is a schematic diagram of an exemplary helizyme.

As used herein, the term helizyme refers to an artificial enzyme in which there is a supporting framework of a plurality of parallel, amphiphilic helical peptides, covalently linked at their carboxyl ends to a multifunctional base framework which holds the helical peptides in a favorable array, some or all of which peptides contain amino acid residues which are found in the active site of the chosen native enzyme, positioned so that a catalytic site can be formed. The structures and interactions of the peptides also allows the formation of a functional substrate binding pocket, with a chosen specificity. The multifunctional base framework is a moiety which contains functional groups to which peptides can be covalently linked or on which peptide chains can be built. It is understood that the base can comprise a single chemical moiety or can be constructed by joining one or more molecules. The base must have a structure that is flexible enough to allow the helices bound thereto to interact to form the desired catalytic site and substrate binding pocket. The peptides of the helizyme must be long enough to allow formation of a helical structure in aqueous solution and to accommodate the desired substrate binding site. Preferably each peptide is from about 10 to about 25 amino acids in length. Hydrophobic and hydrophilic amino acid residues are positioned within the primary sequence of each peptide such that in the preferred α-helical conformation, the helical peptide will have a hydrophilic face and a hydrophobic face. The primary sequence of the peptides is such and the peptides are bound to the base such that the hydrophobic faces of the amphiphilic helices can interact in the interior of the helizyme and the hydrophilic faces of the helices are on the external surface of the helizyme in the preferred conformation in aqueous solution. Hydrophobic interactions of the hydrophobic faces of the component peptides help stabilize the tertiary structure of the helizyme and to generate the functional conformation of the artificial enzyme in aqueous media. The compositions, secondary structures and interactions of the peptides in the helizyme are chosen such that the geometry of the active site amino acids approximates that of the active site of a chosen native enzyme. The helizyme will have at least one catalytic activity of the native enzyme, the active site of which is modeled in the helizyme. The substrate specificity of the helizyme is modified by appropriate choice of amino acid residues in the substrate binding pocket. In general, the substrate binding pocket will have a hydrophobic environment. The substrate binding pocket can be designed to have the specificity of the enzyme on which the active site of the helizyme is modeled. The size, shape and chemical environment of the binding pocket can be modified by introduction of amino acids with desired size and chemical properties into the helical peptides so that they are positioned in the substrate binding pocket. The helical conformation of the peptides and the basic helizyme structure should, however, be maintained. A schematic structure of a generic helizyme is exemplified in FIG. 1.

One or more of the helical peptides of the helizyme can be employed as a platform for the binding of ancillary molecules which are involved in catalysis in addition to the active site amino acids. For example, enzyme co-factors, such as pyridoxal phosphate or flavins, can be attached to the peptides such that they can intact with bound substrate and active site to facilitate reaction. It is understood that the binding of such ancillary molecules must be done without substantially changing the geometry of the helizyme active site or disruption of the substrate binding pocket.

The helizymes of the present invention can also include functionality which allow them to be covalently linked to a solid support material. Such linkage can be achieved by any means known to the art so long as the catalytic function of the helizyme is not disrupted. Solid support materials suitable for the immobilization of enzymes are known in the art. Solid supports suitable for use in the immobilization of the helizymes of the present invention include amino-functionalized polymers or membranes. As helizymes can contain a number of basic amino acid residues, it is important to select the support material and reaction conditions for linking the helizyme to the support to minimize or avoid cross-linking of the helizymes. To avoid such cross-linking and inactivation of the helizyme, it is preferable to employ a solid support having an amino group with a suitable low pK, for example those of aromatic amines and to maintain the pH of the reaction medium lower than about pH 7.0. The skilled artisan will appreciate and understand that various means for modifying the spacer group at the base of the helizyme molecule exist and can be employed. The skilled artisan will also understand how to vary reaction conditions as appropriate for the use of various solid support materials.

In general, it is believed that the structural concept of the helizyme can be employed to model any enzyme active site. Certain classes of proteases, including the serine, thiol or acid proteases, are particularly suitable for modeling by the methods of the present invention.

Members of the serine protease enzyme family contain uniquely reactive serine residues in their active sites; those serine residues react irreversibly with organophosphates such as diisopropyl fluorophosphate causing enzyme inactivation. The active sites of at least three members of the serine protease family exhibit a common tertiary structure at the catalytic site: chymotrypsin, trypsin and elastase. They have similar kinetic properties: they hydrolyze peptides and synthetic ester substrates with pH optima around pH 7.8, and exhibit decreased activities at lower pH values. In each case during the reaction, an acylenzyme intermediate is formed in which the carboxyl group of the substrate is esterified with the hydroxyl of the active site serine.

The amino acids associated with the active site of the serine proteases (aspartate, histidine and serine) form a charge relay system. In chymotrypsin the amino acids of the active site, which form the charge relay system (numbered according to position in the chymotrypsin primary sequence) are Asp-102, His-57, Ser-195 and Ser-214. As determined by X-ray crystallographic analysis, these amino acids are located in approximately the same plane. It is believed that a hydrogen bond is formed between the amido —NH— of the substrate and the carbonyl oxygen of Ser-214. The carbonyl carbon of the substrate is in van der Waals contact with the Ser-195 oxygen. His-57 is believed to act as an acid-base catalyst to assist in the removal of a proton from the hydroxyl group of Ser-195, or from water, thereby increasing the nucleophilicity of that hydroxyl and His 57 then can act as a proton donor to the leaving group of the substrate. In addition, the buried negative charge of the Asp-102 also makes contributions to the nucleophilicity of the Ser-19 hydroxyl oxygen.

Certain bacterial serine proteases, such as subtilisin and *Streptomyces griseus* elastase, have the same charge relay system even though the primary structures of the enzymes are very different from those of the mammalian serine proteases. A similar charge relay system is present in acetyl choline esterase, which has a catalytic mechanism for the hydrolysis of acetyl choline essentially identical to that of ester hydrolysis by the serine proteases.

The serine proteases differ in specificity due to differences in the amino acids associated with the substrate binding pockets. Trypsin is specific for peptides and esters of the basic amino acids lysine and arginine; an aspartate in the substrate binding pocket forms a salt bridge with the positively charged ammonium and guanidinium groups of lysine and arginine. Chymotrypsin recognizes peptides and esters of the aromatic amino acids tryptophan, phenylalanine and tyrosine; it has a hydrophobic substrate binding pocket, and two glycines at the mouth of the substrate binding pocket allow the entry of the bulky aromatic side chains. Elastase specifically cleaves peptides and esters of small hydrophobic amino acids such as alanine; valine and threonine at the mouth of the substrate binding pocket block the entry of bulky side chains on the substrate molecule. Acetyl choline esterase is specific for the substrate acetyl choline ($CH_3COOCH_2CH_2N^+(CH_3)_3$).

In vivo, chymotrypsin is an enzyme of the digestive system. It catalyzes the hydrolysis of peptide bonds in proteins, cleaving adjacent to the carboxyl group of an aromatic amino acid (Phe, Trp, Tyr) or another large hydrophobic amino acid (e.g., Leu, Met). Chymotrypsin also catalyzes the hydrolysis of amides and esters of aromatic amino acids and certain other hydrophobic compounds. Examples of experimental chymotrypsin substrates include N-acetyl-L-phenylalanine amide, N-acetyl-L-tyrosine ethyl ester, N-benzyloxycarbonyl-L-tyrosine p-nitrophenyl ester and N-benzoyl-L-tyrosine ethyl ester.

Chymotrypsin esterase activity can be schematically expressed as follows:

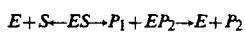

$$E + S \leftrightarrow ES \rightarrow P_1 + EP_2 \rightarrow E + P_2$$

where E is enzyme, S is substrate, ES is the reversible enzyme-substrate complex, $P_1$ is the first product (the leaving group of the substrate), and $P_2$ is the second (carboxylic acid) product. $EP_2$ represents the acylated enzyme intermediate. In the esterase reaction, deacylation of the enzyme is believed to be the rate-limiting step. By contrast, in amide hydrolysis it is believed that the acylation of the enzyme (formation of $EP_2$) is slower than the deacylation step.

Proteases can be classified into four groups, the serine proteases, as discussed above, the thiol proteases, the acid proteases and zinc-containing carboxypeptidases. Of these the thiol, serine and acid proteases are related in that they are endopeptidases. The carboxypeptidases are exopeptidases and are further distinguished from the other classes of proteases as metallo-enzymes.

Thiol proteases include plant enzymes (papain, ficin and bromelain), as well as bacterial and mammalian enzymes. Thiol proteases, as exemplified by papain, are believed to hydrolyze esters and peptides through an acylenzyme mechanism similar to that of serine proteases except that the reaction proceeds via a Cys residue (Cys-25 in papain). In addition to the Cys, a His and an Asp residue compose the active site. Thiol protease activity can be achieved in a helizyme in which the Cys, His and Asp catalytic amino acids are incorporated into helical peptide chains such that the approximate geometry of the active site of the native thiol protease is maintained. The number and composition of the helices and the type of base moiety employed are chosen to achieve the desired active site geometry and allow formation of a substrate pocket by interaction of the helices.

The acid proteases, exemplified by pepsin, function at low pH. The mechanism of catalysis by these enzymes, while believed to proceed via an acyl enzyme as in the serine and thiol proteases, is more complex than in the other proteases. It is known that the active site of the enzyme contains two Asp residues (at positions 32 and 215 in pepsin). Acid protease activity can be achieved in a helizyme in which the Asp catalytic amino acids are incorporated into helical peptide chains such that the approximate geometry of the active site of the native acid protease is maintained. The number and composition of the helices and the type of base moiety employed are chosen to achieve the desired active site geometry and allow formation of a substrate pocket by interaction of the helices.

Chymohelizyme is the term given to a helizyme with at least one catalytic activity and a substrate specificity similar to that of α-chymotrypsin. In the specific embodiment which is Chymohelizyme 1, there are four nonidentical helical peptides linked to a base comprising ornithine and lysine. The structure of the molecule is given in Table 2. Three of the peptides have aspartate, serine and histidine (the serine protease catalytic residues) at their amino termini respectively; the fourth peptide terminates in glutamate. The glutamate pep-tide serves to create an oxyanion hole necessary for catalytic activity and to stabilize the helizyme structure and complete the binding pocket. (Helizyme component peptide chains are named for their amino terminal residues: Glu, His, Asp, Ser.) CHZ-1 was designed with the aid of a commercially available computer program (using MENDYL energy minimization routines) which allows modeling of protein and peptide secondary and tertiary structure (preferred conformations in aqueous solution) from amino acid sequence. The length, composition and number of peptides were adjusted so that the catalytic residues at the N-termini of the peptides would have the geometry of the active site of chymotrypsin. The peptides were designed to be amphiphilic and create a hydrophobic substrate binding pocket in the preferred conformation. The positioning of amino acids in the peptides was also adjusted so that the substrate binding pocket could accommodate a bulky aromatic side chain, e.g., the acetyltyrosine residue of the artificial chymotrypsin substrate acetyl-tyrosine ethyl ester (ATEE). The N-terminal amino acids of each of the peptides was acylated to increase helix stability. A positively charged residue was positioned near the carboxyl end of each helix and a negatively charged residue was placed near the amino end of each helix to effect a favorable interaction with the helix dipole. The secondary structure of each peptide was further stabilized by Glu and Lys residues which provided vertical intrachain ionic bonds between each turn of the helix and interchain ionic bonds laterally between helices. The base moiety, in this case ornithine, was selected allow the attached helices to assume the desired structure in aqueous solution. The single C-terminal residue (Orn) was blocked with the amide function, also to promote helix formation. Application of the "leucine zipper" principle (Landschutz et al. (1988) Science 240:1759–1764) conferred high stability to the hydrophobic core of CHZ-1.

Tryptihelizyme and Cholihelizyme are terms given to helizymes with at least one catalytic activity of and substrate specificity similar to trypsin and acetyl choline esterase, respectively.

Figure 2A:
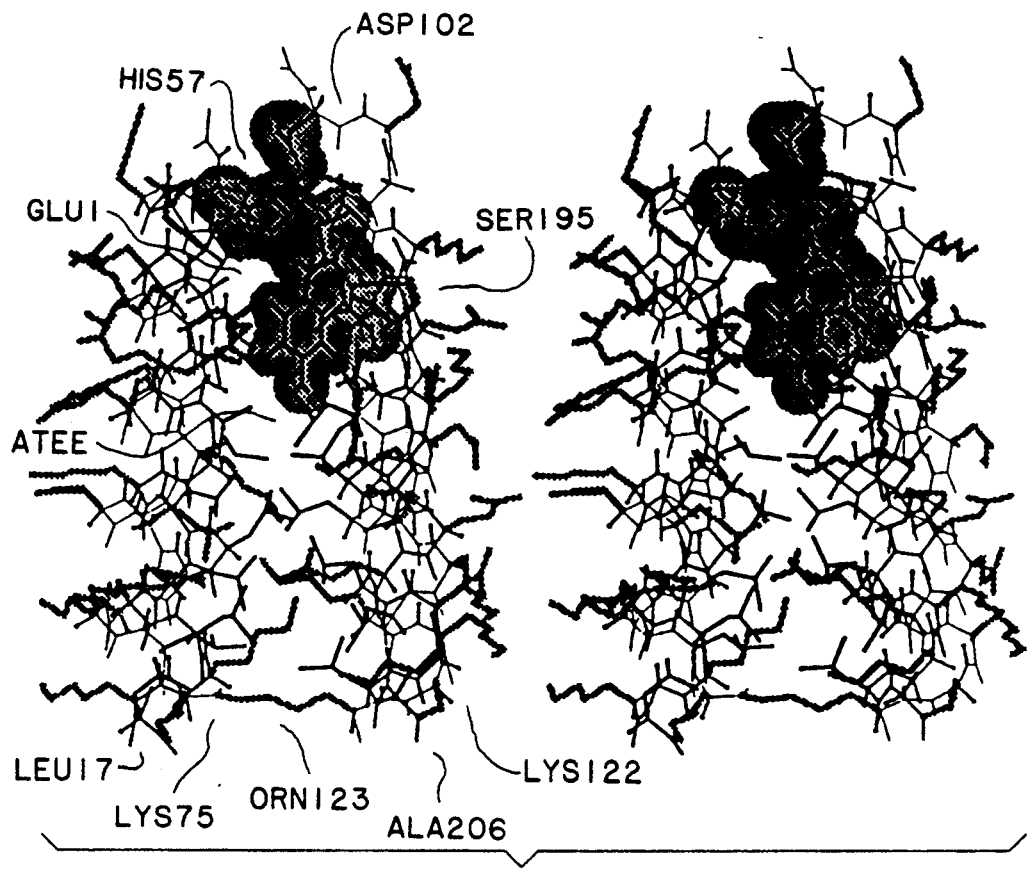
FIG. 2 gives the predicted preferred conformation of Chymohelizyme 1 in aqueous solution as relaxed stereo drawings of "Chymohelizyme 1" structure. Internal hydrophobic side chains are dark and heavy; external polar side chains are broad, light and stippled. Helix backbone chains and N-terminal acetyl groups are in narrow lines. Hydrogen atoms are shown only on α carbons, backbone nitrogens and the substrate; backbone hydrogens are shown as small "knobs" to aid in following the helix. The substrate, acetyl tyrosine ethyl ester (ATEE), is docked in the active site of the enzyme.
Figure 2B:
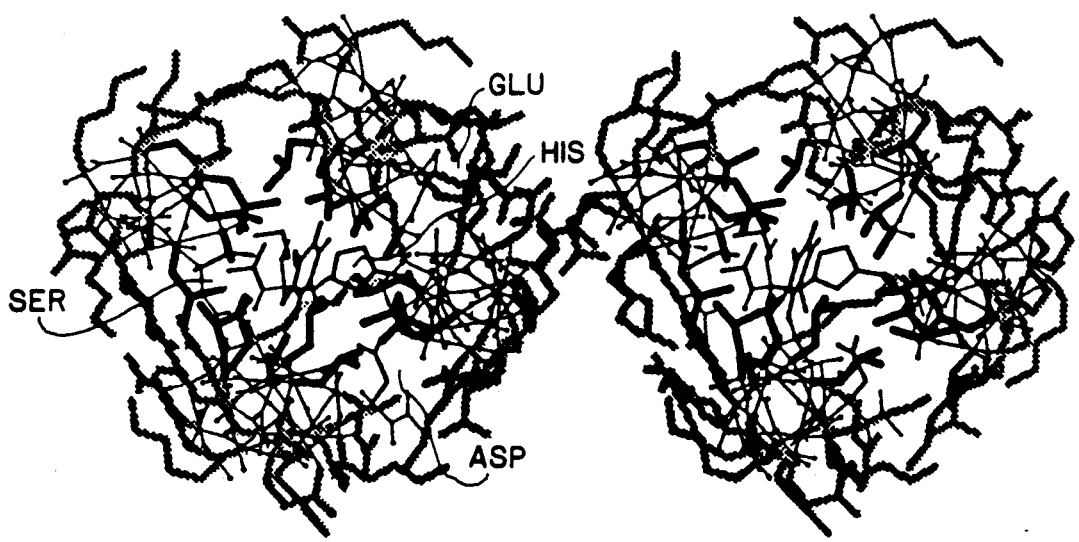

Chymohelizyme 1 displays esterase activity against N-acetyl-L-tyrosine ethyl ester (ATEE), N-benzoyl-L-tyrosine ethyl ester (BTEE) and N-benzyloxycarbonyl-L-tyrosine p-nitrophenyl ester (ZTONP), as does native chymotrypsin. The predicted tertiary structure of the CHZ-1 molecule in aqueous solution is presented in FIG. 2.

The free functional group of the Orn residue at the base of the molecule can also be modified to provide linkage to a solid support via a spacer, so that an immobilized chymohelizyme can be produced. An example of such a modified Chymohelizyme is presented in Table 4. Treatment of CHZ-2 with cyanogen bromide converts the methionine residue to a homoserine lactone. This reactive group can then be linked to a suitable amine-functionalized solid support, such as an amine-activated Sepharose.

In specific embodiments, helizymes were assembled on a methylbenzhydrylamine (MBHA) resin in one operation by automatic solid phase peptide synthesis (SPPS) using a Beckman Model 990B automatic peptide synthesizer (Palo Alto, Calif.). It is understood in the art that there are other suitable peptide synthetic devices, and that manual peptide synthesis can also be performed to produce a helizyme of the present invention. The general principles of SPPS used are described in Stewart and Young (1984) Solid Phase Peptide Synthesis, Pierce Chemical Corporation, Rockford, Ill. These principles were modified as is understood in the art to conform to the best known contemporary practice. Note that abbreviated terms (amino acids, blocking groups) are defined in Table I. Boc, Fmoc and Npys groups are used to protect amino groups in various steps of the synthesis, as needed for specificity. The use of the Npys protecting group in peptide synthesis has been described (Matsueda et al. (1980) Int. J. Peptide Protein Res. 16:392–401). Except in the assembly of the C-terminal linker structure of Lys and Orn, benzyl-related side chain blocking groups were used; these blocking groups were removed simultaneously with the cleavage of the peptide from the resin with HF. Coupling reactions were monitored at nearly all steps using qualitative and quantitative ninhydrin reactions. The use of such techniques as the "chaotropic salt method" maximized effective coupling reactions at each step for peptides having significant secondary structure. The progress of synthesis was monitored at appropriate intervals by removing aliquots of resin for HF cleavage, hydrolysis and amino acid analysis.

Initial purification of the final crude helizyme was effected by ultrafiltration followed by chromatography on a calibrated Sephadex G-50 TM column in 30% acetic acid. The synthesis product consisted primarily of two peaks, with elution patterns consistent with monomer and dimer. Dimerization was observed, and probably was the result of the hydrophobic interactions of two sheet arrays of helices in an extended flat conformation. Final purification was by chromatography on Sephadex LH-60 TM.

Purified Chymohelizyme 1 shows significant helical structure as determined by molar ellipticity at 222 nm in circular dichroism (CD) spectroscopy. In water, CD studies indicated that Chymohelizyme 1 had about 60% helical structure, while in 0.05 M aqueous NaCl solution the molecules had about 80% helical structure. In similar CD studies in 90% (v/v) aqueous ethanol, Chymohelizyme 1 was found to be nearly fully helical.

Kinetic studies of purified Chymohelizyme 1 were performed using ATEE, BTEE or ZTONP as the substrate. Analysis of the initial rates of substrate hydrolysis showed that Chymohelizyme 1 had 2.5% the activity of native α-chymotrypsin for hydrolysis of ZTONP. Native chymotrypsin had a turnover number of 300/sec while Chymotrypsin 1 had an initial turnover number of about 6–8/sec. A rapid decline in the enzyme turnover number was observed, evidently due to inhibition of enzyme activity by the reaction product p-nitrophenol.

Purified Chymohelizyme 1 showed esterase activity for BTEE and ZTONP over a range of pH values. There was a broad optimum around pH 8.5 for BTEE, as measured in 50 mM Tris-Cl, 50 mM sucrose, 9% dioxane. For ZTONP hydrolysis, as measured in 50 mM Tris-Cl buffer, peak activity appeared to be at about pH 9, with almost no activity at around pH 10.3.

Hydrolysis of ATEE at pH 8.1 in 0.05 molar sodium chloride solution followed classical Michaelis-Menten kinetics; kM=1.0 mM and kcat=0.042/sec (corresponding values for chymotrypsin are 0.7 mM; 3.0/sec), showing an activity approximately 1% that of chymotrypsin for this substrate.

It was found that hydrolysis of substrates by the monomeric Chymohelizyme 1 is inhibited by indole and p-cresol, which are specific inhibitors of chymotrypsin. Inclusion of indole at a concentration equal to that of the substrate ZTONP caused approximately 70% inhibition of substrate hydrolysis.

Hydrolysis of substrates by Chymohelizyme 1 showed inactivation by heat, as is characteristic of natural enzymes. In contrast to natural enzymes, however, heat-inactivated CHZ-1 reassumed the correct catalytically active conformation after it is cooled, dissolved in glacial acetic acid and lyophilized.

Chymohelizyme 1 showed esterase activity against the artificial chymotrypsin substrates ATEE, BTEE and ZTONP. The chymotrypsin-like activity for the synthetic Chymohelizyme 1 with artificial substrates showed that the molecule assumes the secondary and tertiary structure necessary to place the active site residues in the proper three-dimensional arrangement for catalytic activity and to constitute a functional substrate binding site. There was no esterase activity observed when the artificial substrate benzoyl-arginine ethyl ester (BAEE) was used as the substrate. BAEE is a substrate for trypsin, but not for chymotrypsin, thus demonstrating the selectivity of CHZ-1.

The structure of Chymohelizyme 2 is shown in Table 3. In Chymohelizyme 1 noncovalent forces stabilize the tertiary structure assumed by the four helical peptides. A potential disadvantage of Chymohelizyme 1 is a tendency to associate to form inactive dimers, depending on the salt composition of the aqueous solution. In Chymohelizyme 2, a disulfide bond between Cys residues in the Glu and Ser peptides gives added stability to the association of the four peptides in the monomeric conformation.

Similar principles were applied in the design of a Tryptihelizyme 1, a synthetic enzyme with the activity and specificity of trypsin. The amino acid sequence of Tryptihelizyme 1 is given in Table 4. A peptide structure similar to that of a Chymohelizyme was employed, but the substrate binding pocket has a negatively charged amino acid residue to stabilize the binding of the side chains of arginine or lysine in the substrate molecule. As with the Chymohelizyme, the active site residues are present in a substantially planar configuration and in relative positions which mimic the arrangement of active site residues in the native trypsin enzyme.

Similar principles were also applied to the design of Cholihelizyme 1, the amino acid sequence of which is presented in Table 5. The binding pocket of Cholihelizyme 1 includes amino acid residues which stabilize the binding of acetyl choline.

It is understood in the art that modifications may be made to the primary structures of specific Chymohelizymes, Tryptihelizymes or Cholihelizymes, disclosed herein, without destroying their chymotrypsin-like, trypsin-like or acetyl choline esterase-like activities. For example, it is possible that a substitution may be made in the structure of one or more of the helical peptides without significantly affecting the structure of the molecule. Further, it is possible that certain amino acid substitutions may need to be compensated by another change in the sequence of the same peptide or in one or more of the other peptides in order to maintain the desired structure. Similarly, it is possible that additional amino acids may be added to the amino-terminal amino acid of one or more of the component peptides of a helizyme of the present invention without destroying substrate binding or catalytic activity. It will be understood that it is not only the actual primary sequences of the component peptides or identity of the multifunctional base moiety which determines a functional helizyme. Functionality of a helizyme results from the overall design of a molecule having a tertiary structure, having certain features as described herein, by which a functional substrate binding site and catalytic site appropriate for the desired catalytic activity and substrate specificity are created.

The skilled artisan understands that manipulating the salt content of an aqueous solution or modifying the organic solvent content of a substantially aqueous solution can effect the favored conformation of the helizyme and thus, can affect the kinetics of the reaction. The more compact structure of the helizyme, as shown in FIG. 1, is believed to be optimal for catalysis; therefore, it is believed that the milieu of the enzyme should be adjusted so that maximum helicity of the peptides is obtained for best enzymatic activity.

It will be appreciated by those of ordinary skill in the art that the objects of this invention can be achieved without the expense of undue experimentation using well known variants, modifications, or equivalents of the methods and techniques described herein. The skilled artisan will also appreciate that alternative means, other than those specifically described, are available in the art to achieve the structural features of the catalytic peptide molecules described herein and how to employ those alternatives to achieve functional equivalents of the catalytic molecules of the present invention. It is intended that the present invention include those variants, modifications, alternatives and equivalents which are appreciated by the skilled artisan and encompassed by the spirit and scope of the present disclosure.

The following examples are intended to illustrate the invention only, and are not intended to limit the scope of the invention.

EXAMPLE 1

Design of Chymohelizyme 1

The Silicon Graphics (Mountain View, California) IRIS system for molecular modeling and the SYBYL-MENDYL software package from Tripos (St. Louis, Mo.) provided a computerized system for molecular design. The Brookhaven Laboratories database for protein structures as determined by X-ray crystallography is publicly available. All the chymotrypsin structures available in the database were considered in the selection of active site parameters. The active site residues of chymotrypsin were marked and the remainder of the protein structure was removed, leaving 20 the active site residues in three dimensional space. The four peptide sequences of each CHZ-1 and CHZ-2 were then designed to maintain the desired three dimensional structure of the active site in the helizyme molecules. In both CHZ-1 and CHZ-2, the Ser, His and Asp catalytic amino acids were positioned in different helical peptides and a fourth peptide, ending in a Glu residue, supplied the "oxyanion hole" feature and completed the substrate binding site and stabilized the overall structure of interacting amphiphilic helices.

MENDYL energy minimization routines were used to assure that the bond angles and contact points incorporated into the helizymes were realistic and that the molecule had a high probability of assuming the desired conformation spontaneously in aqueous solution.

Synthesis of Chymohelizyme 1

The amphiphilic helical peptide segments of desired lengths between 15 and 22 amino acids were assembled into the appropriate branched structure using automatic SPPS using methods as described in Stewart and Young (1984) *Solid Phase Peptide Synthesis*, Pierce Chemical Company, Rockford, Ill.). To synthesize Chymohelizyme 1, a Beckman (Palo Alto, Calif.) Model 990B automatic peptide synthesizer was used.

To assemble the structure of Chymohelizyme 1, (Table 2), the starting material was Boc-Orn(Fmoc)-MBHA-Resin (abbreviations for amino acids and blocking groups and conventions for use of these abbreviations are given in Table 1). Orn, in which the α-amino group was blocked with t-butyloxycarbonyl (Boc) and the delta amino group was blocked with 9-fluorenylmethoxycarbonyl (Fmoc), was attached to MBHA resin.

To begin the synthesis, the Boc group was deprotected with TFA-DCM, and Npys-Lys(Boc) was coupled to the α-amino group of the Orn bound to the resin.

Next, the Boc group on the lysine was deprotected and Boc-Ala was coupled to the epsilon-amino group of the Lys on the resin complex, to yield a branched chain.

To synthesize the chain bearing the amino-terminal Ac-Asp residue (the Asp chain) ending in Lys-Orn at the carboxyl terminus, the Npys blocking group was removed from the Lys residue with triphenyl phosphine, and the next amino acid in the chain (Lys) was added. All α-amino groups of residues in this chain were protected with the Npys group. Asp and Glu side chains were blocked with benzyl (Bzl) blocking groups and Lys side chains were blocked with 2-chlorobenzyloxycarbonyl (Clz) blocking groups.

After the N-terminal Asp residue (Asp-102) was added and the Npys group removed, the amino terminus was blocked by acetylation with acetyl imidazole.

To build the Ser chain of the helizyme, the Boc group on the alanine (Ala-209) was deprotected and amino acids were sequentially added as Boc derivatives. Side chains were blocked as before. The amino group of the N-terminal serine (Ser-195) was acetylated as above.

To synthesize the His chain, the Fmoc group on the Orn was deprotected and Boc-Lys (Npys) was added. The Npys group was deprotected and Npys-Ala was added. The His chain was assembled using Boc o protection. Following acetylation of His-57, the Glu chain was assembled using Boc protection.

Peptide Cleavage and Purification

The peptide was cleaved from the peptide-resin complex (600 mg) by treatment with liquid hydrogen fluoride (20 ml) in the presence of p-cresol (5%) and thioanisole (5%) at 0° C. for one hour. The liquid was evaporated under vacuum. The residue was washed once with 20 ml ethyl acetate and three times with ethyl ether. The peptide was extracted with 10% aqueous acetic acid (60 ml). The solution was diluted to 200 ml with water and ultrafiltered using a YM-5 Amicon membrane; this process was repeated three times to remove all low molecular weight impurities. The final solution was lyophilized, with a yield of 217.8 mg. 109 mg of peptide was dissolved in water, treated with decolorizing carbon at 60° C., filtered and the filtrate lyophilized, to yield 90.9 mg of decolorized peptide.

The decolorized peptide (21 mg) was chromatographed on a LH-60 Sephadex TM column (60 cm/2.5 cm) and eluted with 70% ethanol. The peptide appeared as one major peak at an elution volume of about 215 ml and one minor peak at an elution volume of about 240 ml. 20.57 mg of peptide was recovered from the major peak and 2.21 mg of material was recovered from the side peak.

The peptide recovered from the major peak from the LH-60 column was further purified by gel filtration on a G-50 Sephadex TM (50 cm/1.5cm) column using 20% acetic acid as the solvent. The lyophilized product showed the correct amino acid composition upon hydrolysis and analysis of an aliquot.

Assay of Chymohelizyme 1

Hydrolysis of BTEE and ZTONP were performed as described (Meth. Enzymol. volume XIX, Academic Press, New York, 1970, pp. 38–41). The progress of the reaction was followed spectrophotometrically. Progress of the hydrolysis of ATEE was followed by titration.

Hydrolysis of the trypsin substrate benzoyl arginine ethyl ester (BAEE) was tested as described (Meth. Enzymol. ibid., pp. 41–43).

EXAMPLE 2

Design of Chymohelizyme 2

Chymohelizyme 2 was designed as a modification of Chymohelizyme 1. The sequence of this molecule is given in Table 3. The tertiary structure is such that the active site amino acid residues (Ser, His and Asp) are positioned in different peptides in a substantially planar geometric array which mimics that of native chymotrypsin. As in Chymohelizyme 1, the fourth peptide has Glu at its N-terminus. The Glu peptide serves to stabilize the helizyme structure and to create the oxyanion hole which facilitates the reaction. The synthetic CHZ-2 shown in Table 6 contains the carboxy terminal modification to permit immobilization by attachment to a solid support.

The Glu and Ser peptide chain sequences were changed so that in the helizyme molecule, a Cys residue in each of those two peptides is positioned so that a disulfide bond can form, thus giving added stability to the tertiary structure of the Chymohelizyme 2 molecule as compared with that of Chymohelizyme 1. This structure is less likely to form dimers in aqueous solutions; thus, the useful lifetime of Chymohelizyme 2 is expected to be greater than that of Chymohelizyme 1.

We claim:

1. A helizyme molecule having the primary structure

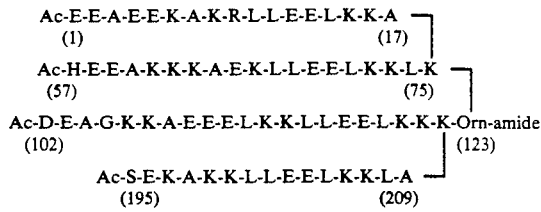

2. A helizyme molecule having the primary structure

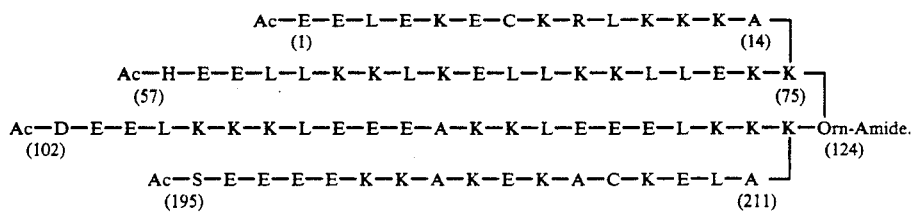

3. A helizyme molecule having a primary structure selected from the group consisting of

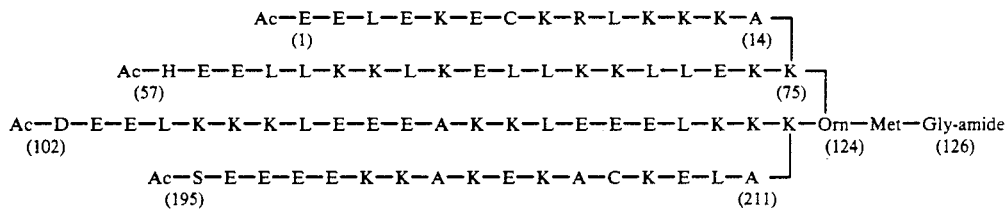

and

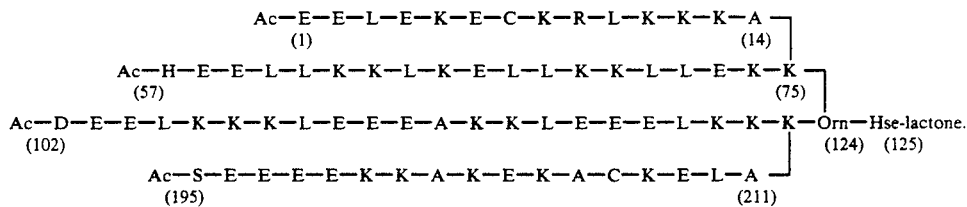

4. A helizyme molecule having a primary structure which is

5. A helizyme molecule having a primary structure which is

```
Ac—E—E—A—E—E—K—A—K—R—L—L—E—E—L—K—K—A ┐
   (1)                                    (17) │
Ac—H—E—E—A—K—K—K—A—E—K—L—L—E—E—L—K—K—L—K ┤
   (57)                                       (75)
Ac—D—E—A—G—K—K—A—E—E—L—K—K—L—L—E—E—L—K—K—K—Orn-amide.
   (102)                                           (123)
      Ac—S—E—K—A—K—K—L—L—E—E—L—K—K—L—A ┘
         (195)                          (209)
```

\* \* \* \* \*

UNITED STATES PATENT AND TRADEMARK OFFICE
CERTIFICATE OF CORRECTION

PATENT NO. : 5,304,631
DATED : April 19, 1994
INVENTOR(S) : Stewart, et. al.

It is certified that error appears in the above-indentified patent and that said Letters Patent is hereby corrected as shown below:

Column 19, lines 20 and 21, delete and close the gap between "leaving" and "the"; delete 20--.
Column 23, first line of text, replace the first "L" with --D--.

Signed and Sealed this

Eleventh Day of October, 1994

Attest:

BRUCE LEHMAN

Attesting Officer        Commissioner of Patents and Trademarks